United States Patent [19]

Gleave

[11] Patent Number: 4,477,436

[45] Date of Patent: Oct. 16, 1984

[54] COMPOSITION FOR AND A METHOD OF TREATING HAIR AND/OR SCALPS

[76] Inventor: Dorothy Gleave, 33 Chatsworth Rd., St. Annes-on-Sea, Lancashire, England

[21] Appl. No.: 484,963

[22] Filed: Apr. 14, 1983

Related U.S. Application Data

[63] Continuation of Ser. No. 325,966, Nov. 30, 1981, abandoned.

[30] Foreign Application Priority Data

Feb. 12, 1980 [GB] United Kingdom ............... 8038551

[51] Int. Cl.$^3$ ............................................. A61K 35/12
[52] U.S. Cl. .................................................... 424/95
[58] Field of Search ......................................... 424/95

[56] References Cited

PUBLICATIONS

Chemical Abstracts (1982) vol. 97.

Primary Examiner—Elbert L. Roberts
Attorney, Agent, or Firm—Quaintance & Murphy

[57] ABSTRACT

A composition for treating hair and/or scalps of human beings consists of a mixture of protein, vegetable oil, hydrocarbons, alcohol, emulsifying agents and keratin fibre strengthener. The composition in the form of a cream is applied to and massaged into the hair and/or scalp at least once in each twenty four hour period, each period of massage being of at least fifteen minutes duration.

5 Claims, No Drawings

COMPOSITION FOR AND A METHOD OF TREATING HAIR AND/OR SCALPS

This is a continuation of application Ser. No. 325,966 filed Nov. 30, 1981, now abandoned.

This invention relates to a composition for and a method of treating hair and/or scalps and more particularly, to a composition for and a method of treating hair and/or scalps of human beings which is capable of improving the health and strength of existing hair on a human scalp.

According to one aspect of this invention, a composition for treating hair and/or scalps of human beings comprises a mixture of protein, a skin softening and penetrating substance, a hydrocarbon, alcohol, and an emulsifying substance.

Preferably, the mixture includes a keratin fibre strengthener and the strengthener may comprise rosemary. Preferably, also, the skin softening and penetrating substance comprises a vegetable oil such as, for example, castor oil.

Preferably, the composition comprises 20 to 40% by weight protein, 10 to 30% by weight vegetable oil, 1 to 5% by weight hydrocarbon, 20 to 40% by weight alcohol, 1 to 10% by weight emulsifying substance and 1 to 15% by weight rosemary.

Preferably, the protein comprises beef bone marrow and the composition may comprise 32.79% by weight beef bone marrow, 21.68% by weight castor oil, 2.64% by weight paraffin oil, 28.91% by weight rum, 5.78% by weight emulsifying white wax and 8.20% by weight rosemary.

According to another aspect of this invention, a method of treating hair and/or scalps comprises applying the composition according to said one aspect of this invention to the hair and/or scalp, and massaging the composition into the hair and/or scalp.

Preferably, the composition is applied to and massaged into the hair and/or scalp at least once during each twenty four hour period and each massage is continued for at least fifteen minutes.

In a preferred embodiment of this invention, a composition for treating human hair and/or scalps comprises by weight 20 to 40% protein, 10 to 30% vegetable oil, 1 to 5% hydrocarbon, 20 to 40% alcohol, 1 to 10% emulsifying substance and 1.15% keratin fibre strengthener.

The protein is an active ingredient and one particularly suitable protein has been found to be beef bone marrow. The vegetable oil acts as a skin softening and penetrating substance and here again, it has been found that castor oil is particularly suitable although it is envisaged that other alternative vegetable oils could be used such as, for example, olive oil or almond oil.

The hydrocarbon utilised in the composition is paraffin oil and the alcohol is rum but it is envisaged that other alternative hydrocarbons and alcohols could be utilised without departing from the scope of this invention. In addition, one particularly suitable emulsifying substance has been found to be emulsifying white wax but here again it is envisaged that other emulsifying agents could be utilised.

One particularly suitable specific composition consists of 28.35 grammes of beef bone marrow, 18.75 grammes of castor oil, 2.28 grammes of paraffin oil, 25.00 grammes of rum, 5.00 grammes of emulsifying white wax, and 7.09 grammes of rosemary.

The composition is manufactured by pouring the castor oil into a mixing vessel and adding the beef bone marrow thereto. The castor oil and the beef bone marrow are mixed until they reach a creamy consistuency and the rosemary is then added and stirred into the mixture. The mixing vessel is then heated by, for example, placing the mixing vessel over a container of boiling water and the emulsifying white wax is then added and stirred into the mixture until the wax is dissolved. The mixing vessel is then allowed to cool to room temperature and the rum is then added. The paraffin oil is then added to the mixture one drop at a time whereupon the composition is thoroughly stirred and is left in the mixing vessel for a period of at least four hours before the composition is removed therefrom and packaged into individual airtight containers or jars.

The composition which is in the form of a cream is applied to the hair and/or scalp and is thoroughly massaged into the hair and scalp for a period of at least fifteen minutes. It has been found to be beneficial for the composition to be applied and massaged into the hair and the scalp at least once during each twenty four hour period and preferably, the treatment is continued for at least seven days or longer to obtain the most beneficial effects.

It has been found that the application of this composition improves the health and strength of existing hair on a human scalp.

I claim:

1. A composition comprising 20 to 40% by weight beef bone marrow, 10 to 30% by weight castor oil, 1 to 5% by weight paraffin oil, 20 to 40% by weight rum, 1 to 10% by weight emulsifying white wax, and 1 to 15% by weight rosemary.

2. A composition according to claim 1, comprising 32.79% by weight beef bone marrow, 21.68% by weight castor oil, 2.64% by weight paraffin oil, 28.91% by weight rum, 5.78% by weight emulsifying white wax, and 8.20% by weight rosemary.

3. A method of treating hair and/or scalps comprising applying the composition according to claim 1 to the hair and/or scalp, and massaging the composition into the hair and/or scalp.

4. A method according to claim 3, wherein the composition is applied to and massaged into the hair and/or scalp at least once during each 24-hour period and each massage being conducted for at least fifteen minutes.

5. A method of manufacturing a composition suitable for improving the health and strength of existing hair on a human scalp, the composition having the following constituents, by percentage of weight of total ingredients:

beef bone marrow: 32.79%
castor oil: 21.68%
paraffin oil: 2.64%
rum: 28.91%
emulsifying white wax: 5.78%
rosemary: 8.20% said manufacturing method comprising the steps of: pouring the castor oil and beef bone marrow into a mixing vessel; mixing the oil and marrow until a creamy consistuency is reached; adding the rosemary to the mixture and stirring the same; heating the mixture; adding the emulsifying white wax to the mixture and stirring the same until the wax is dissolved; removing the mixture from heat and cooling the same to room temperature; adding the paraffin oil and thoroughly stirring the mixture; leaving the mixture to stand in the mixing vessel for at least four hours; removing the mixture from the mixing vessel; and packaging of the mixture in airtight container means.

* * * * *